US00PP30563P2

(12) United States Plant Patent
Egger

(10) Patent No.: US PP30,563 P2
(45) Date of Patent: Jun. 4, 2019

(54) ***XHEUCHERELLA* PLANT NAMED 'SPICY LIME'**

(50) Latin Name: ***xHeucherella* hybrid**
Varietal Denomination: Spicy Lime

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/998,093

(22) Filed: Jun. 29, 2018

(51) Int. Cl.
*A01H 5/00* (2018.01)
*A01H 6/80* (2018.01)

(52) U.S. Cl.
USPC ..... Plt./441

(58) Field of Classification Search
USPC ..... Plt./441
See application file for complete search history.

*Primary Examiner* — Annette H Para
(74) *Attorney, Agent, or Firm* — Klarquist Sparkman, LLP

(57) ABSTRACT

A new and distinct x*Heucherella* plant substantially as shown and described, characterized by a low mounding habit, excellent crown count, yellow to lime colored leaves with blotchy deep red markings along veins, medium short wands of very light pink flowers, and excellent vigor.

1 Drawing Sheet

Botanical denomination: x*Heucherella* hybrid.
Variety designation: 'Spicy Lime'.

BACKGROUND OF THE INVENTION

The present invention relates to a new and distinct cultivar of x*Heucherella* and given the cultivar name of 'Spicy Lime'. x*Heucherella* is in the family Saxifragaceae. x*Heucherella* 'Spicy Lime' originated from a controlled cross between two unknown, unnamed, proprietary intergeneric hybrids of *Heuchera* and *Tiarella*.

Compared to x*Heucherella* 'Gold Zebra', U.S. Plant Pat. No. 22,104, the new cultivar has shallower lobes and leaves with less solid red patterning along veins.

Compared to x*Heucherella* 'Hot Spot', U.S. Plant Pat. No. 27,417, the new cultivar has a low mounding habit rather than a spreading habit, *Tiarella*-like leaf shape, and medium short wands of very light pink flowers instead of showy dark pink flowers.

Compared to x*Heucherella* 'Mojito' U.S. Plant Pat. No. 26,946, the new cultivar has light pink flowers instead of white, and leaves with less red patterning along veins.

This new x*Heucherella* is uniquely characterized by:

1. low mounding habit,
2. excellent crown count,
3. yellow to lime colored leaves with blotchy deep red markings along veins,
4. medium short wands of very light pink flowers, and
5. excellent vigor.

This new cultivar has been reproduced only by asexual propagation (cuttings and tissue culture using growing points at the crown). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a three-year-old plant growing in a gallon container in part shade in early June in Canby, Oreg.

DETAILED PLANT DESCRIPTION

The following is a detailed description of the new x*Heucherella* cultivar based on observations of three-year-old specimens grown in gallon pots in part shade mid-June in Canby, Oreg. Canby is Zone 8 on the USDA Hardiness map. Temperatures range from a high of 95 degrees F. in August to an average of 32 degrees F. in January. Normal rainfall in Canby is 42.8 inches per year. The color descriptions are all based on *The Royal Horticultural Society Colour Chart,* $5^{th}$ edition, 2007.

Plant:

*Type*.—Herbaceous perennial.
*Form*.—Basal rosette.
*Hardiness*.—USDA Zone 4 to 9.
*Size*.—22 cm tall from top of the foliage to the ground and 47 cm wide.
*Habit*.—Mounding with 30 crowns.
*Vigor*.—Excellent.
*Roots*.—Fibrous, freely branching, fine and White 155A in color.

Leaf:

*Type*.—Simple.
*Arrangement*.—Rosette.
*Shape*.—Broadly ovate.
*Number*.—180.
*Blade size*.—Grow to 10 cm long and 9.7 cm wide.
*Lobing/division*.—5 main palmate divisions cut ½ of the way to the main vein each with secondary lobes cut to ⅓-⅛ to the secondary veins.

*Venation*.—Palmate.
*Margins*.—Broadly crenate and slightly undulate.
*Apex*.—Obtuse to mucronulate.
*Base*.—Cordate, overlapping.
*Surface texture*.—Glandular hairs on both surfaces.
*Leaf rugosity*.—Weak.
*Leaf undulation*.—Low-moderate.
*Glossiness*.—Weak.
*Petiole description*.—Grows to 18.4 cm long and 2.3 mm wide, bottom ⅔ between Greyed Red 181B and Greyed Red 181C, fading to Green White 157C near leaf attachment, with glandular hairs.
*Leaf color*.—New leaves; topside between Yellow Green 144B and Green 142B with blotchy pattern along veins Greyed Purple 183A, bottom side between Green 141D and Green 142C including veins with, mature leaves; topside between Yellow 12B and Yellow 12C including veins with blotchy pattern along veins Orange Red N34A, bottom side Yellow 11B with veins Yellow 11C.

Inflorescence:
*Size*.—Usually 8 cm long and 2 mm wide.
*Type*.—Upright raceme.
*Number of racemes*.—About 28.
*Number of flowers per raceme*.—About 40.
*Density of flowers in raceme*.—Loose.
*Peduncle*.—Grows to 18 cm long, 2.5 mm wide at base.
*Pedicel*.—Grows to 5 mm long, with glandular hairs, Red 49D.
*Bloom period*.—May through June in Canby, Oreg.

Flower bud:
*Size*.—3 mm long and 2 mm wide.
*Description*.—Glandular puberulent, ovoid, down to side-facing.
*Color*.—Red 49B.

Flower:
*Type*.—Perfect.
*Shape*.—Campanulate.
*Attitude*.—Side-facing.
*Size*.—5 mm deep and 5.2 mm wide.
*Petal description*.—5 in number, stellate, spatulate, 2.3 mm long and 1 mm wide, tip acuminate, base attenuate, margin entire, glabrous and White NN155A on both sides.
*Calyx description*.—5 mm deep and 5.2 mm wide, campanulate, with 5 lobes, divided ½ way to the base, lobes 2 mm long and 1.5 mm wide, oblong, glandular hairs on both sides, tip obtuse, margin entire, Red 36B on both sides with tips Red 48C.
*Stamen description*.—10, 3 mm long, filament 3 mm long and White NN155B, anthers White NN155B, no pollen.
*Pistil description*.—1 in number, grows to 4 mm long and 2 mm wide, ovaries grow to 2 mm long and 2.5 wide, White NN155B, beaked style 2 mm long, White NN155B.
*Fragrance*.—None.
*Lastingness*.—Each raceme blooms for about 2 weeks on the plant.

Fruit and seed: None.

Disease and pest tolerance: The new cultivar is typical to the genus. No known resistances to pests or diseases. No problems have been found in Canby, Oreg.

I claim:

1. A new and distinct x*Heucherella* plant as herein illustrated and described.

* * * * *

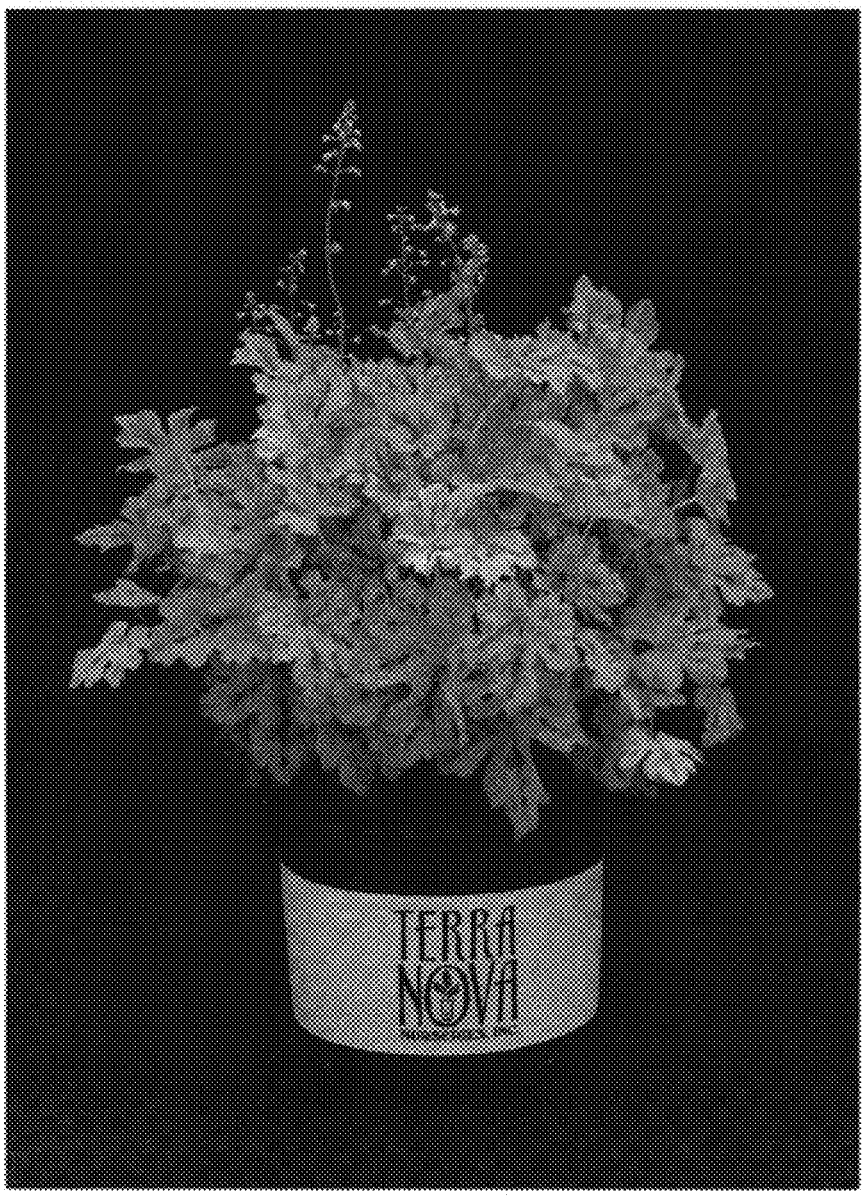
TERRA
NOVA